United States Patent
McCalmont et al.

(10) Patent No.: US 12,042,251 B2
(45) Date of Patent: Jul. 23, 2024

(54) SYSTEMS AND METHODS OF ARRHYTHMIA DETECTION

(71) Applicant: BraveHeart Wireless Inc., Nashua, NH (US)

(72) Inventors: Stephen A. McCalmont, Hollis, NH (US); Stuart P. MacEachern, Hopkinton, MA (US); Ralph L. Beck, Sterling, MA (US); Anthony Falcone, Hollis, NH (US)

(73) Assignee: BraveHeart Wireless Inc., Nashua, NH (US)

( * ) Notice: Subject to any disclaimer, the term of this patent is extended or adjusted under 35 U.S.C. 154(b) by 732 days.

(21) Appl. No.: 16/857,625

(22) Filed: Apr. 24, 2020

(65) Prior Publication Data

US 2020/0337567 A1    Oct. 29, 2020

Related U.S. Application Data

(60) Provisional application No. 62/837,812, filed on Apr. 24, 2019.

(51) Int. Cl.
*A61B 5/00* (2006.01)
*A61B 5/0205* (2006.01)
*A61B 5/352* (2021.01)
*A61B 5/366* (2021.01)

(52) U.S. Cl.
CPC ........ *A61B 5/02055* (2013.01); *A61B 5/0022* (2013.01); *A61B 5/352* (2021.01); *A61B 5/366* (2021.01); *A61B 5/6802* (2013.01); *A61B 5/7264* (2013.01); *A61B 5/0024* (2013.01); *A61B 2562/02* (2013.01)

(58) Field of Classification Search
None
See application file for complete search history.

(56) References Cited

U.S. PATENT DOCUMENTS

| | | | | |
|---|---|---|---|---|
| 7,697,983 B1* | 4/2010 | Oza | ........................ | A61N 1/025 607/5 |
| 9,468,386 B2* | 10/2016 | Braojos Lopez | ...... | A61B 5/349 |
| 10,426,364 B2* | 10/2019 | Rapin | .................... | G16H 50/30 |
| 10,758,139 B2* | 9/2020 | Rapin | .................... | G16H 50/30 |
| 2013/0157883 A1* | 6/2013 | Keller | .................. | C12Q 1/6883 536/24.31 |
| 2015/0057512 A1* | 2/2015 | Kapoor | .............. | A61B 5/02405 600/513 |
| 2015/0257668 A1* | 9/2015 | Braojos Lopez | ...... | A61B 5/349 600/512 |

(Continued)

OTHER PUBLICATIONS

"Introduction to Supervised Deep Learning Algorithms!" published May 20, 2021 <https://www.analyticsvidhya.com/blog/2021/05/introduction-to-supervised-deep-learning-algorithms/> accessed on Sep. 12, 2023 (Year: 2021).*

(Continued)

*Primary Examiner* — Shirley X Jian
(74) *Attorney, Agent, or Firm* — Maine Cernota & Curran

(57) ABSTRACT

Systems and methods of arrhythmia detection and associated apparatus that utilize machine learning techniques that allow for the consideration individual characteristics and the tailoring/personalization of biometric data allow for early detection and treatment, especially of cardiac arrhythmias and other abnormalities.

19 Claims, 10 Drawing Sheets

(56) References Cited

U.S. PATENT DOCUMENTS

| | | | |
|---|---|---|---|
| 2016/0199659 A1* | 7/2016 | Jiang | A61N 1/37247 607/60 |
| 2019/0069795 A1* | 3/2019 | Kiranya | G16H 50/20 |
| 2019/0333216 A1* | 10/2019 | Isgum | G06T 7/10 |
| 2019/0347426 A1* | 11/2019 | Coffing | G06F 21/44 |
| 2020/0388391 A1* | 12/2020 | Upton | G16H 50/20 |

OTHER PUBLICATIONS

"Unsupervised Feature Learning and Deep Learning Tutorial: Convolutional Neural Network" published Sep. 27, 2013 <http://deeplearning.stanford.edu/tutorial/supervised/ConvolutionalNeuralNetwork/ > accessed on Sep. 12, 2023 (Year: 2013).*

* cited by examiner

SYSTEMS AND METHODS OF ARRHYTHMIA DETECTION

RELATED APPLICATIONS

This application claims the benefit of the U.S. Provisional Application No. 62/837,812 filed Apr. 24, 2019. This application is herein incorporated by reference in its entirety for all purposes.

FIELD OF THE INVENTION

The invention relates to arrhythmia detection, and, more particularly, to arrhythmia detection methods and systems suitable for use in clinical and non-clinical environments.

BACKGROUND OF THE INVENTION

The wearable medical device market has expanded greatly over the past decade, with consumer devices, such as the Fitbit® and Jawbone® wireless activity trackers, becoming a popular way for people to quantify and take charge of their personal fitness and overall well-being. While these devices are the most visible of their kind to consumers, rapid developments are simultaneously occurring in similar devices having a wide range of clinical uses. These devices are constantly becoming smaller, offering better battery life through both new battery chemistries and more efficient electronics, while providing more data and using better and more efficient algorithms to render that data useful.

As these devices become ubiquitous and more capable, they are being used to as a substitute for time consuming, expensive, and inconvenient hospital testing procedures. This transition has also allowed biometric measurements to be taken over a longer period of time, opening up new testing opportunities and new uses for the longer-term data obtained, notably by allowing for intermittent conditions to be more effectively detected, and thus treated before they become life-threatening. However, much of this data is currently being treated in largely the same way as the more limited data obtained using prior art devices and methods.

What is needed, therefore, are techniques for efficiently utilizing the long-term data obtained from this new breed of clinical and consumer oriented devices in a way that more fully takes advantage of their capabilities and improves detection rates, especially of intermittent conditions that can be elusive during more time-limited testing.

SUMMARY OF THE INVENTION

An objective of embodiments of the present disclosure is to utilize machine learning, including neural nets, support vector machines, deep networks, and the like, as well as other techniques to improve the quality of medical data by tailoring population models to individuals and analyzing biometric signals associated with a patient in real time using, in embodiments, wearable devices that include appropriate sensor packages and sufficient computing resources to analyze biometric signals in real time.

More specifically, by taking advantage of the ergodicity of biological processes, an individual's biological signals over time can be considered the mathematical equivalent of a population at a given time (i.e. the time average is equivalent to the average over a population), enabling the modification of a population model into an individualized model using the techniques further described herein.

A further objective of embodiments of the present disclosure is to provide wearable health sensors that employ such machine learning techniques to improve both the quantity and quality of medical data.

Still another object of embodiments of the present invention is to track and quantify an individual's biometric data over an extended period of time that is not currently feasible using current, state-of-the-art technology.

Still even another object of embodiments of the present invention is to allow for the creation of local and cloud-based repositories of patient data for later review and analysis, thereby providing valuable insights into trends and patient health that might not otherwise be noticeable during routine caregiver visits, while providing medical researchers vast amounts of potentially useful clinical information that may enable medical breakthroughs through, among other potential methods, the application of big data analytics.

A still even further objective of embodiments of the present disclosure is to improve caregiver efficiency by reducing or eliminating the need for the measurement of vital signs during patient visits.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 1:
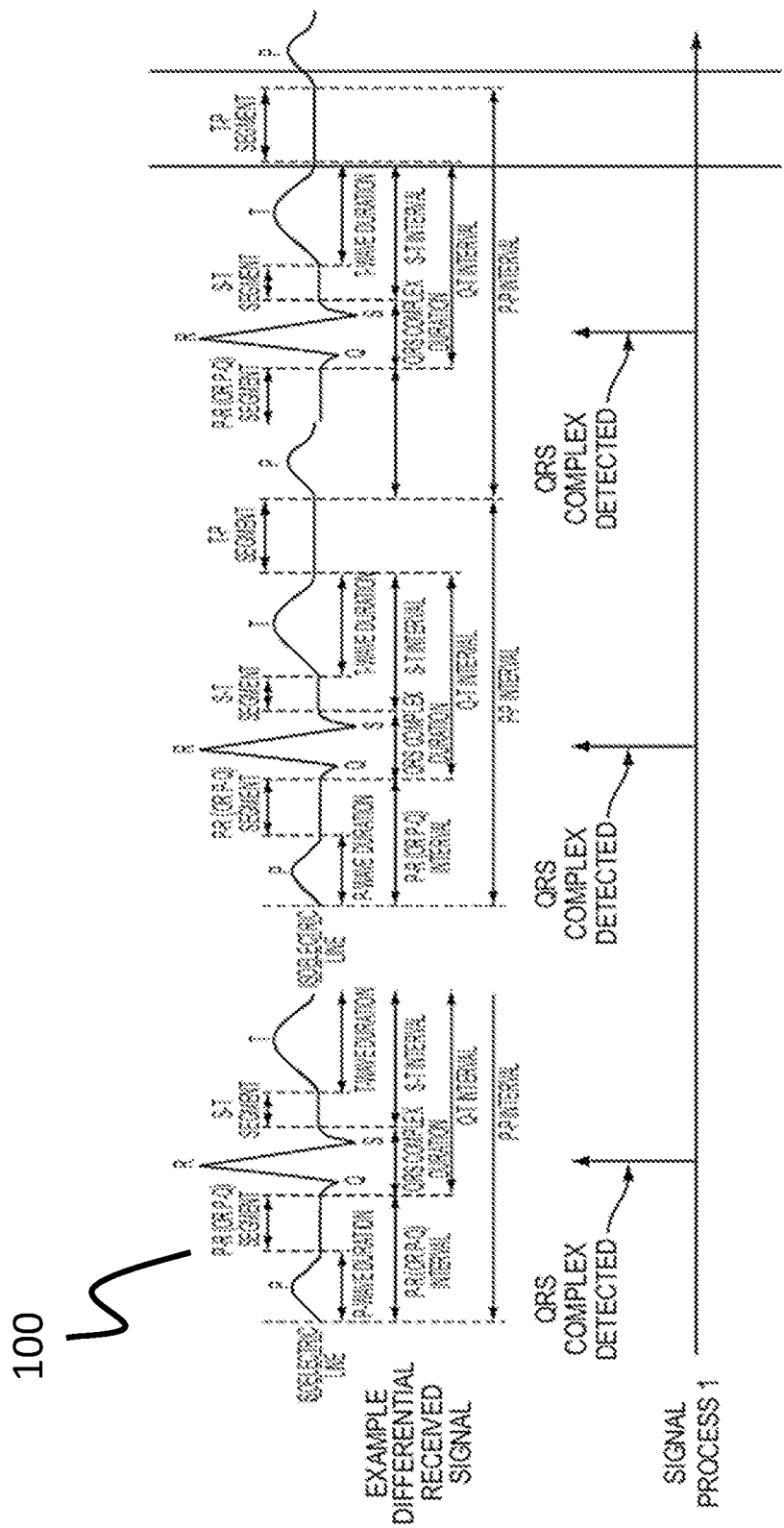
FIG. 1 is a graph showing a repeating QRS complex signal processing, in accordance with embodiments of the present disclosure.
Figure 2:
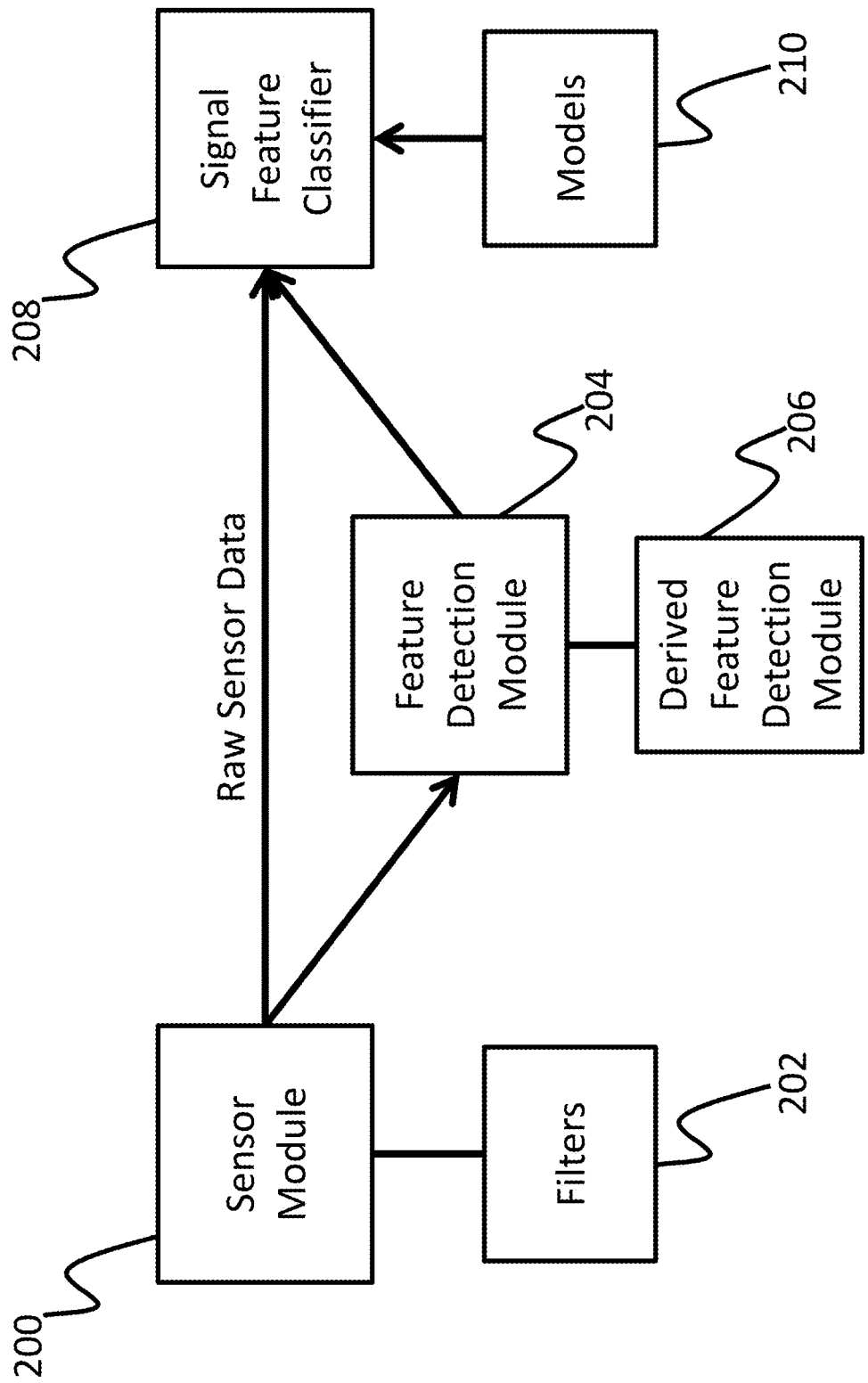
FIG. 2 is a flowchart describing signal, processing, and classification, in accordance with embodiments of the present disclosure.
Figure 3:
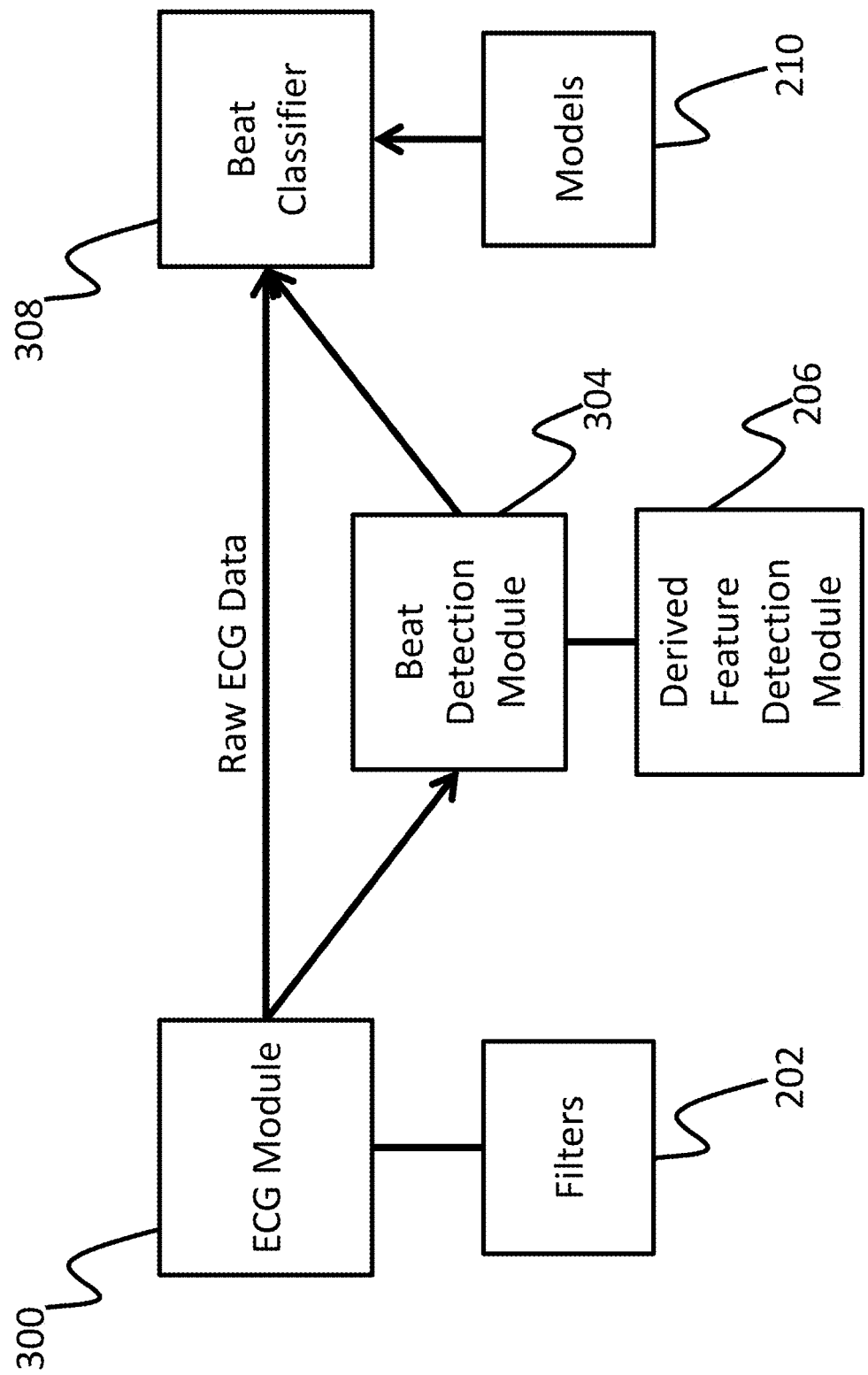
FIG. 3 is a flowchart describing ECG detection, processing, and classification, in accordance with embodiments of the present disclosure.

Now referring to FIG. 1, FIG. 1 comprises a graph showing a QRS complex 100 and processing thereof by a detection and synchronization apparatus, such as the feature detection module 204 shown in FIG. 2 or the beat detection module 304 of FIG. 3, in accordance with embodiments of the present disclosure. In this graph, particularly the example differential received signal portion thereof, it can be seen that the received signal can be broken down into repeating segments, with some segments overlapping. In this case, the repeating signal is an ECG signal 100 and the repeating segments are the PR Interval, PR Segment, QRS Complex, QT Interval, ST Segment, and TP Segment, with specific points on that segment being labeled P, Q, R, S, and T, in order of appearance in the repeated signal.

In embodiments of the present disclosure, such as that depicted in FIG. 2, a biometric signal is received using a sensor module 200 configured to receive such a signal. The raw sensor data 412 is then simultaneously sent to both a feature detection module 204, which, in embodiments, analyzes the signal for repeating segments, and a signal feature classifier 208, which, in embodiments, uses models 210 that take into account data received from the feature detection module 204 and the sensor data to classify a signal (e.g. as normal, abnormal, critical, etc.). More specifically, the signal feature classifier 208, by analyzing the data received from the feature detection module 204 along with the characteristics of the raw signal in the vicinity of any detected features, is able to obtain a more accurate picture of a patient's health.

The feature detection module 204, in embodiments, in in operative communication with a derived feature detection module 306 capable of further analyzing the information generated by the feature detection module 204.

In embodiments, the sensor module 200 also interacts with filters 202 to filter the data obtained thereby prior to its provision to the signal feature classifier 208 and feature detection module 204.

In embodiments, information extracted from additional sensors, such as accelerometers, peripheral capillary oxygen saturation sensors (SpO2 sensors), respiration rate sensors, galvanic skin response sensors, temperature sensors, humidity sensors, light sensors, and the like, are analyzed in parallel with information provided by the signal feature classifier 208 to provide a more complete picture of a patient's overall well-being. This information, in embodiments, is also taken into account by the signal feature classifier 208 during signal classification.

In embodiments, the sensor data may be down-sampled, allowing models to be more parsimonious (i.e. require less storage).

In embodiments, the signal feature classifier 208 also functions as a statistics generator that establishes a baseline characterization of patient response.

In a more specific embodiment, such as that shown in FIG. 3, an ECG signal is received using an ECG module 300 configured to receive an ECG signal. The raw ECG signal, in embodiments a filtered ECG signal, is then sent to a beat detection module 304, which extracts particular features from the ECG signal. For instance, in embodiments the beat detection module 304 analyzes the raw ECG signal for repeating segments, such as a QRS complex 100, as shown in FIG. 1. After this step, an output of the feature detection module 304 (i.e. the extracted feature(s)) as well as the raw and/or filtered ECG signal(s) are both passed to the beat classifier 308.

In embodiments, the derived feature detection module 206 conducts further analysis of the signal to measure various characteristics thereof, such as the R peak of the signal, or can conduct an analysis of the signal to determine various characteristics thereof, such as heart rate variability.

The beat classifier 208, in embodiments, uses models 210 that take into account data received from the beat detection module 304 as well as the raw ECG data to classify an ECG signal (e.g. as normal, abnormal, critical, etc.).

The ECG module itself may also interact with filters 202 to filter the data obtained thereby prior to its provision to the beat classifier 308 and beat detection modules 304 as a form of pre-processing.

In embodiments, information extracted from additional sensors, such as accelerometers, peripheral capillary oxygen saturation sensors (SpO2 sensors), respiration rate sensors, galvanic skin response sensors, temperature sensors, humidity sensors, light sensors, and the like are analyzed in parallel with information provided by the beat classifier 308 to provide a more complete picture of a patient's overall well-being. This information, in embodiments taken into account when classifying a QRS complex 100, as described above.

In embodiments, the ECG data may be down-sampled, allowing models to be more parsimonious (i.e. require less storage).

In embodiments, the beat classifier 308 also functions as a statistics generator that establishes a baseline QRS complex 100 morphology for each patient.

Various embodiments also support data normalization. For instance, where multiple wearable health sensors 100 are used and configured to gather overlapping information, the data may be compared and erroneous data identified and omitted or data averaged to obtain superior accuracy and reduce the transmission of redundant data.

Embodiments may also utilize multiple beat detection modules 304, each relying on different algorithms to detect R peaks, and select the best data from amongst the multiple beat detection modules 304 for provision to the beat classifier 308.

Figure 4:
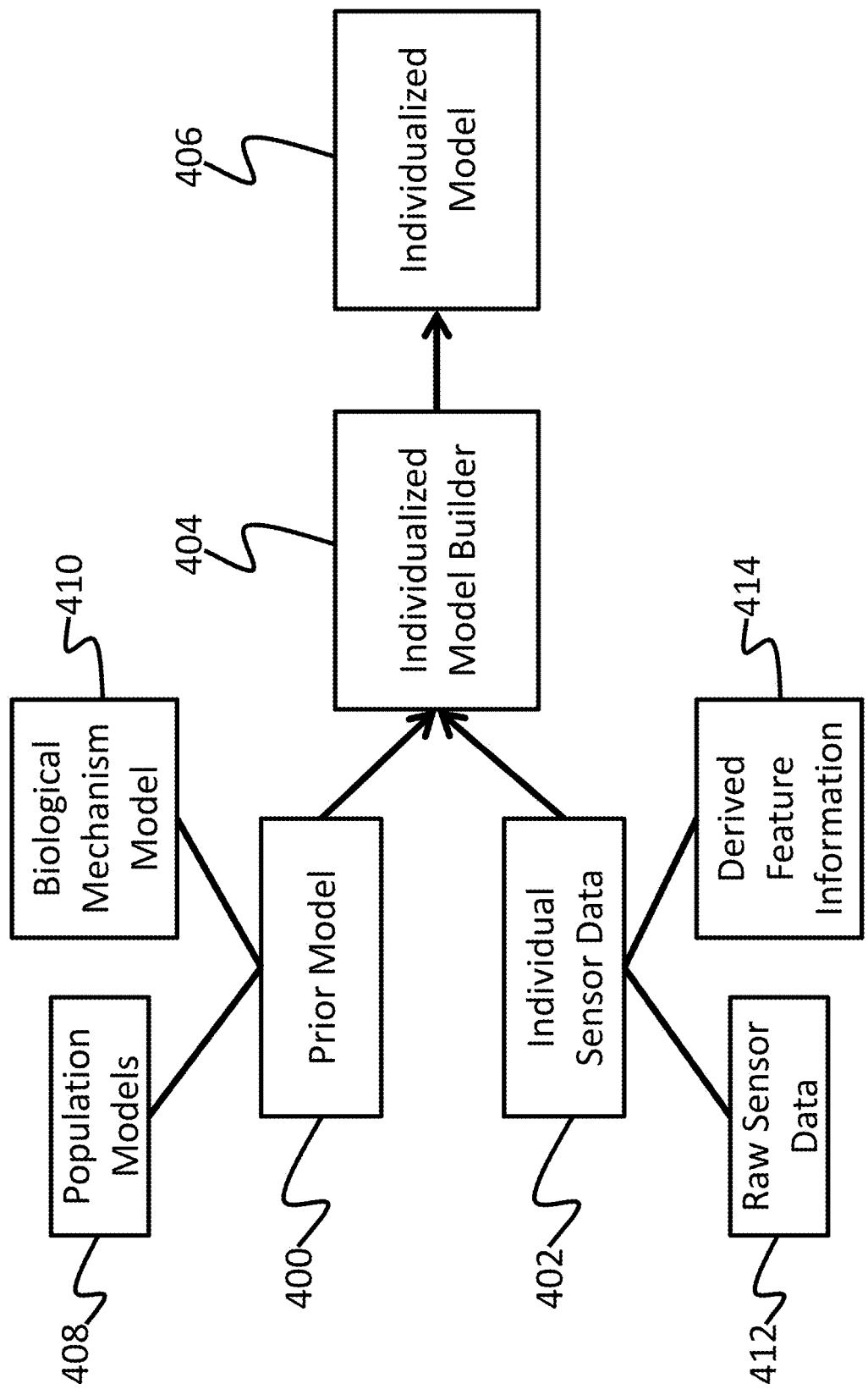
FIG. 4 is a flowchart describing a system for and method of creating an individualized model, in accordance with embodiments of the present disclosure.

Now referring to FIG. 4, a flowchart describing a system for and method of creating an individualized model 406, in accordance with embodiments of the present disclosure is shown. More specifically, an individualized model builder 404 is used to create the individualized model 406. The individualized model builder 404 receives and combines a prior model 400 with individual sensor data 402, in embodiments ECG sensor data, to create the individualized model 406. In embodiments, the prior model 400 comprises both at least one population model 408 and a biological mechanism model 410, such as a heartbeat mechanism model. In embodiments, the individual sensor data 402 comprises raw sensor data 412, such as raw ECG sensor data, as well as derived feature information 414, such as R peak and/or heart rate variability information.

In embodiments, machine learning is used by the individualized model builder 404 to generate an individualized model 406. This machine learning enables algorithms used by signal feature classifier 208 (or beat classifier 308) to be altered on-the-fly, enabling the personalized and rapid detection of abnormal conditions, by better taking into account a particular patient's baseline patterns.

Machine learning, in embodiments, comprises two distinct phases and can work with a stream, a file, or a combination thereof. The first phase is a training phase that may also be referred to as a supervised learning phase. This training phase involves the scoring of matches to models and, in embodiments, takes place offline, prior to deployment, using a population of patient data distinct from any given individual.

For the purposes of this disclosure, online learning refers to learning that occurs as the data comes in, e.g. as a stream, while offline refers to learning that occurs using a static dataset.

During supervised learning, an individual manually labels portions of data (training data) and an algorithm produces an inferred function. The inferred function created based on the training data can be used to map new examples, for instance, as normal or abnormal, without further input from an individual.

The second phase, which may be referred to as an unsupervised learning phase, augments the supervised learning phase and enables individualization of the population based model(s) (e.g. the prior model 400) generated in the first phase. In embodiments, this second phase is an individualized model 406 training phase conducted by the individualized model builder 404, and may be passive (i.e. the user simply goes about their daily routine) or involve the measurement of specific states, such as exercise, rest, etc. (i.e. the user is required to engage in certain activities so that a baseline for each can be established). During this phase, the prior model 400 is combined with individual sensor data 402 by the individualized model builder 404 to develop an individualized model 406.

More specifically, during unsupervised learning, at least one machine learning algorithm and/or technique is used to draw inferences from datasets consisting of individual sensor data 402, including raw sensor data 412 and derived feature information 414, without labeled responses (i.e. the type generated during the supervised learning phase of training in which patterns are scored by individuals, such as doctors).

In embodiments, unsupervised learning, e.g. cluster analysis, is used to find hidden patterns or grouping in the data that might not be readily apparent to a medical practitioner, given such a practitioner's limited ability to analyze the vast quantity of data that may be required to identify the pattern and/or the subtlety thereof and, furthermore, their complete inability to do so in real-time.

In embodiments, inferences are drawn by comparing individual sensor data 402 to an individualized model 406 in real time.

In embodiments, particular classifications are given a score based on their match to a particular model, allowing a medical practitioner to review the most important data in a timely fashion.

In embodiments, machine learning utilizes non-parametric Bayesian methods, which make use of make use of infinite-dimensional mathematical structures.

In embodiments, stochastic models are used. A stochastic model is realized in the form of a conditional probability, to be contrasted with the use of a conditional expectation. In the latter, inputs are used to compute a single output, usually a maximum likelihood estimate, or some similar statistic, using well-established mathematical techniques, as would be known to one of ordinary skill in the art. Conversely, the use of conditional probabilities, in embodiments, enables a user to associate to a given set of inputs a probability distribution over the collection of all possible outputs. Consequently, conditional probabilities produce posterior distributions that allow for more informed subsequent analysis.

In embodiments, the models generated by (online, real time) unsupervised learning can be considered similar to a fingerprint, in that they are unique to an individual and somewhat dynamic over a person's lifetime. As such, these models can be used to identify an individual, allowing the individual to securely access programs, data, and other media without the need for a password, or in addition thereto, as a form of two-factor authentication.

Figure 5:
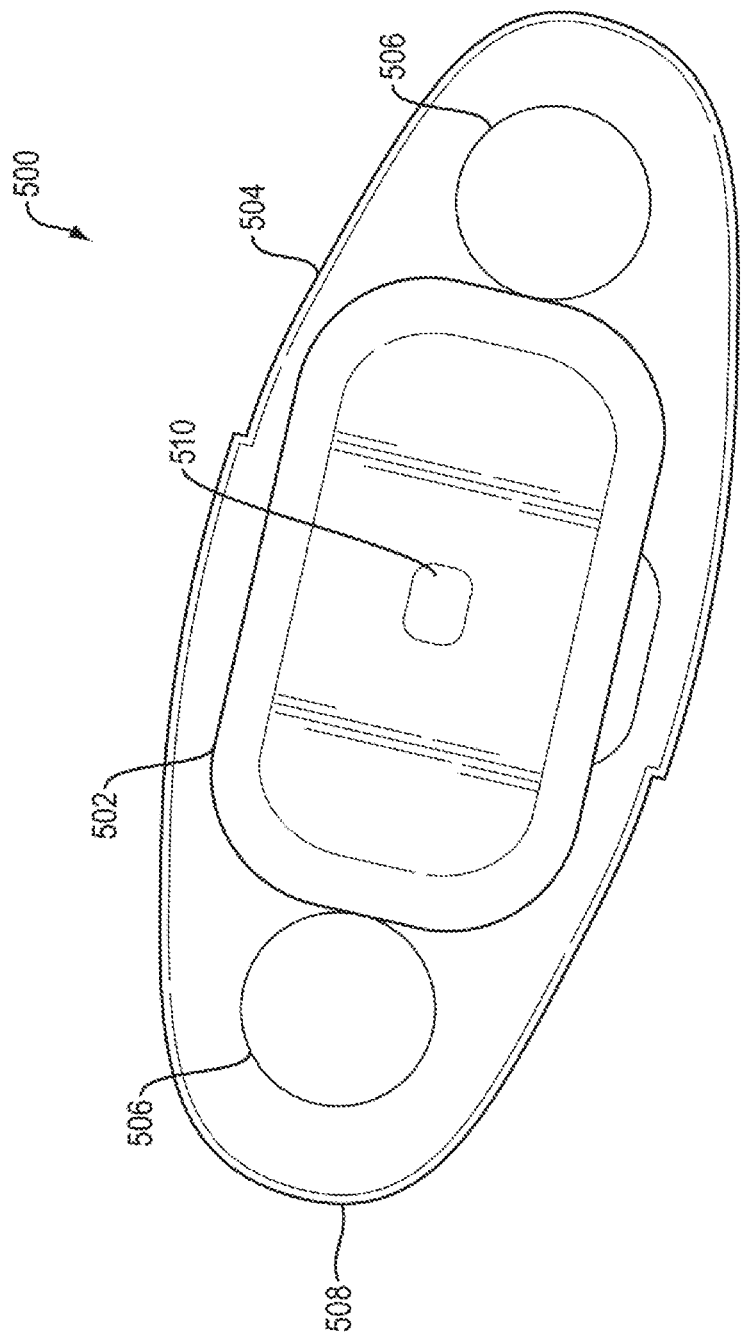
FIG. 5 is a top, elevation view of a wearable health sensor, configured in accordance with embodiments of the present disclosure.

Now referring to FIG. 5, a top, elevation view of a wearable health sensor 500, configured in accordance with embodiments of the present disclosure, is shown. The wearable health sensor 500 includes a housing 502 containing circuitry necessary to the operation of the sensor. The wearable health sensor 500 further comprises a mounting strip 504, in embodiments similar in size and shape to a medium sized adhesive bandage, onto which the housing 502 can be affixed. The mounting strip 404 is used to attach the housing 502 to a user and, in embodiments, comprises an adhesive layer disposed opposite the housing 502 such that the mounting strip 504 may be removably attached to a user in any convenient location.

In embodiments, the mounting strip comprises electrodes 506 in operative communication with the housing 502, when affixed to the mounting strip 504, allowing circuitry contained therein to use the electrodes to monitor biometric data of a user therethrough.

In embodiments, the mounting strip 504 comprises a release liner 508 disposed on the adhesive portion(s) thereof, to ensure the adhesive is not contaminated prior to use.

In embodiments, the housing 502 is reusable and contains a power supply. The power supply, in embodiments, is a rechargeable battery that may be recharged using inductive charging technology, a charging port, or other charging technologies, as would be known to one of ordinary skill in the art. In other embodiments, an internal disposable battery is user-replaceable. In still other embodiments, a capacitor is used as a power source, enabling rapid charging.

In embodiments, the housing 502 comprises a function button 510, which can be programmed to perform a variety of functions, as necessary or desired. For example, the function button 510 can allow a user to identify times at which they feel symptoms of a potential arrhythmia and result in a marking of the data preceding and following the button press for review by a medical practitioner and/or for consideration by unsupervised learning algorithms.

Figure 6A:
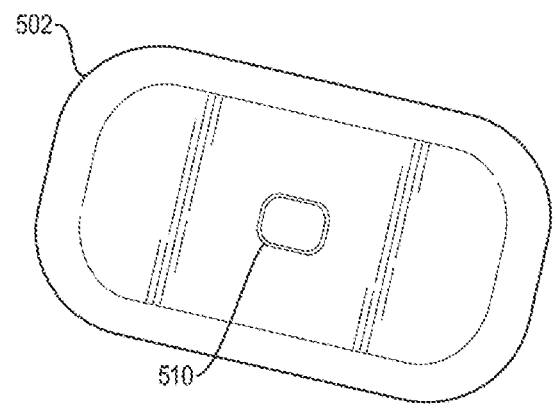
FIG. 6A is a top, elevation view of the circuitry-containing portion of a wearable health sensor, in accordance with embodiments of the present disclosure.

Now referring to FIG. 6A, a top, elevation view of the circuitry-containing portion of a wearable health sensor 500, in accordance with embodiments of the present disclosure, is shown.

Figure 6B:
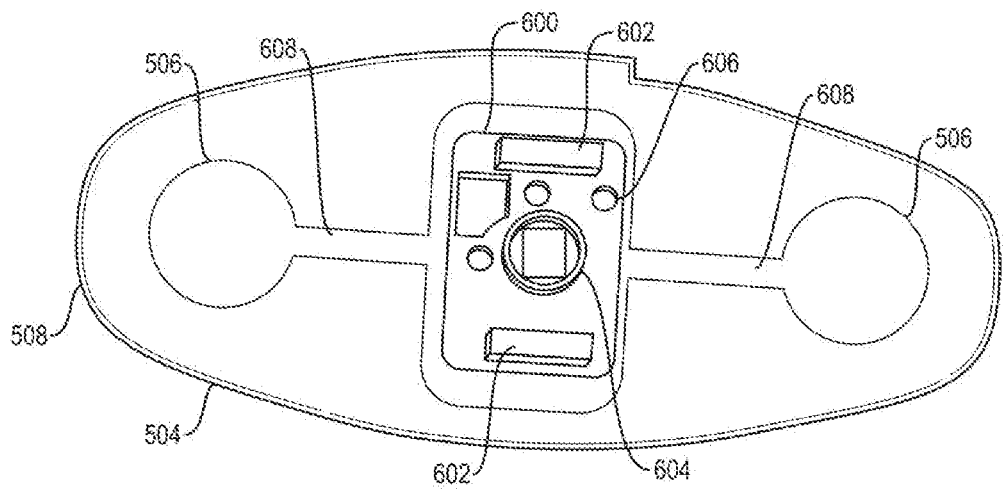
FIG. 6B is a top, elevation view of the adhesive portion of a wearable health sensor, in accordance with embodiments of the present disclosure.

FIG. 6B shows a top, elevation view of a mounting strip 504, in accordance with embodiments of the present disclosure, wherein the housing 502 has been removed therefrom. From this figure, it can be seen that the mounting strip comprises a relatively narrow spine 600 that is disposed substantially centrally on the mounting strip 504. Furthermore, the spine comprises a connector 604 disposed substantially centrally thereon. The connector 512 is configured to provide electrical connectivity between the housing 502 and mounting strip 504, which, in embodiments, contains a variety of sensors (e.g. electrodes 506) and/or pass-throughs for sensors contained within the housing 502.

For example, in embodiments, apertures 606 in the spine 600 of mounting strip 504 align with Light Emitting Diodes (LEDs) disposed on the bottom of the housing 502, allowing for the measurement of oxygen saturation in a user. In embodiments, three apertures 608 are used to enable three frequency blood oxygen saturation measurement.

In embodiments, fiber optic wires, fiber optic cables, light pipes, and/or similar light-conveying means are disposed in the mounting strip 504 and positioned to align with light-emitting elements in the housing 502. Many additional sensor types could be used in conjunction with the wearable health sensor 500 described herein, as would be known to one of ordinary skill in the art.

In embodiments, the mounting strip 504 utilizes magnets 602 to secure the housing 502 thereto, utilizing corresponding magnetic materials disposed in the housing 502. In embodiments, these magnets 602 are phased magnets 602 that act to repel the housing 502 from the mounting strip 504 if the orientation of the two is incorrect (i.e. 180° off), discouraging users from assembling the components incorrectly.

The spine 600 is, in embodiments, connected to electrodes through flexible connections 608, which may be wires, traces, or other types of flexible connections, as would be known to one of ordinary skill in the art.

Figure 7A:
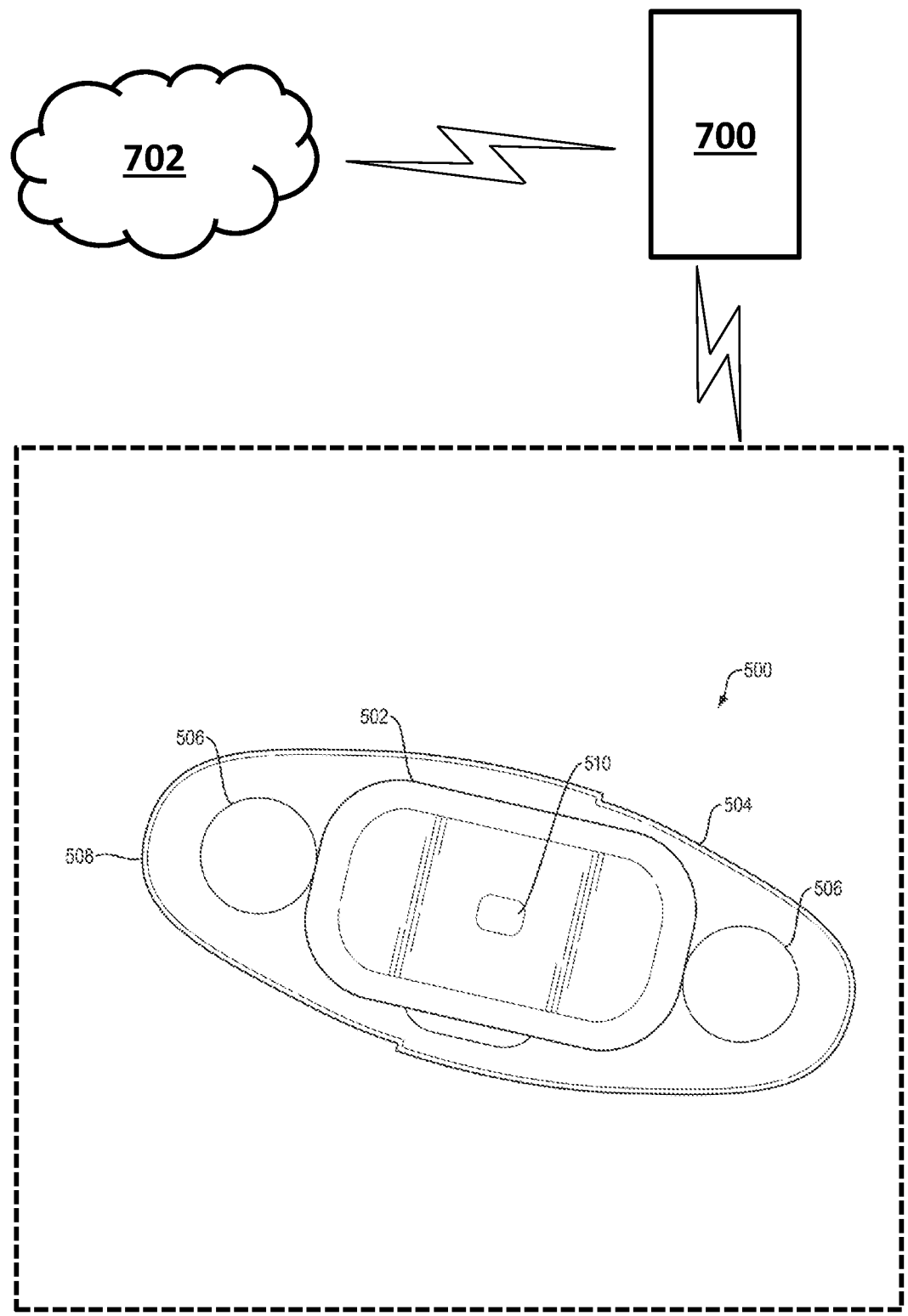
FIG. 7A is a depiction of a wearable health sensor in operative communication with a network, through a user device, in accordance with embodiments of the present disclosure.

Now referring to FIG. 7A, wearable health sensor 500 is shown in operative communication with a network-enabled device 700, which may, in embodiments, be in further communication with a network 702. In embodiments, this network 702 may be a local-area network, such as might be used in a hospital setting for intra-hospital communications, while in other embodiments this network 702 may be a wide-area network, such as the internet.

Figure 7B:
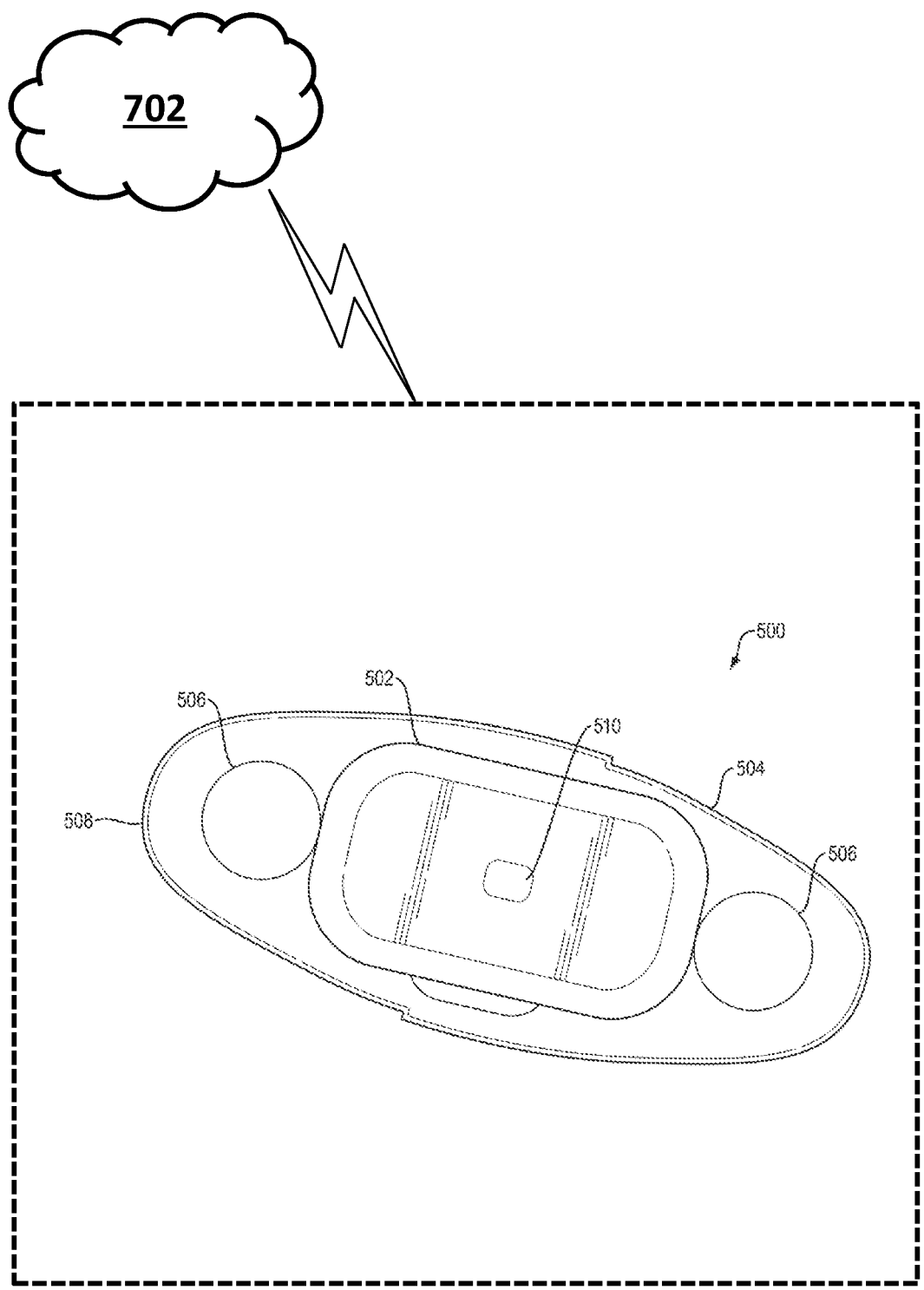
FIG. 7B is a depiction of a wearable health sensor in operative communication with a network, in accordance with embodiments of the present disclosure.

Now referring to FIG. 7B, a wearable health sensor 500 is shown in operative communication directly with a network 702, in accordance with embodiments of the present disclosure.

Figure 8A:
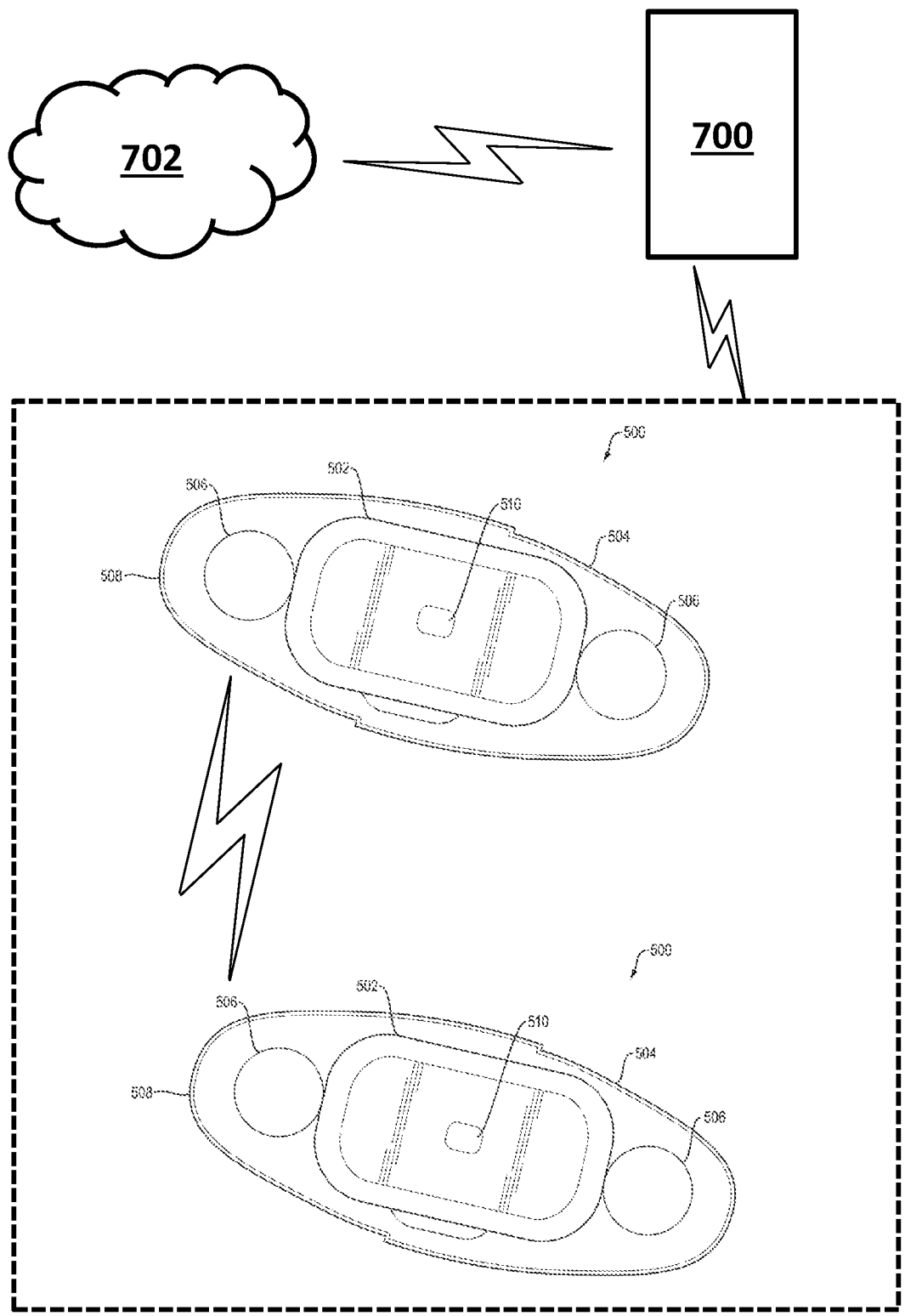
FIG. 8A is a depiction of two wearable health sensors in operative communication with one another and in further operative communication with a network, through a user device, in accordance with embodiments of the present disclosure.

Now referring to FIG. 8A, two wearable health sensors 500 are shown in operative communication with one another, allowing them to share data and otherwise capture data that a single sensor could not, and in further operative communication with a network-enabled device 700, which may, in embodiments, be in further communication with a network 702. In embodiments, this network 702 may be a local-area network, such as might be used in a hospital setting for intra-hospital communications, while in other embodiments this network 702 may be a wide-area network, such as the internet.

Figure 8B:
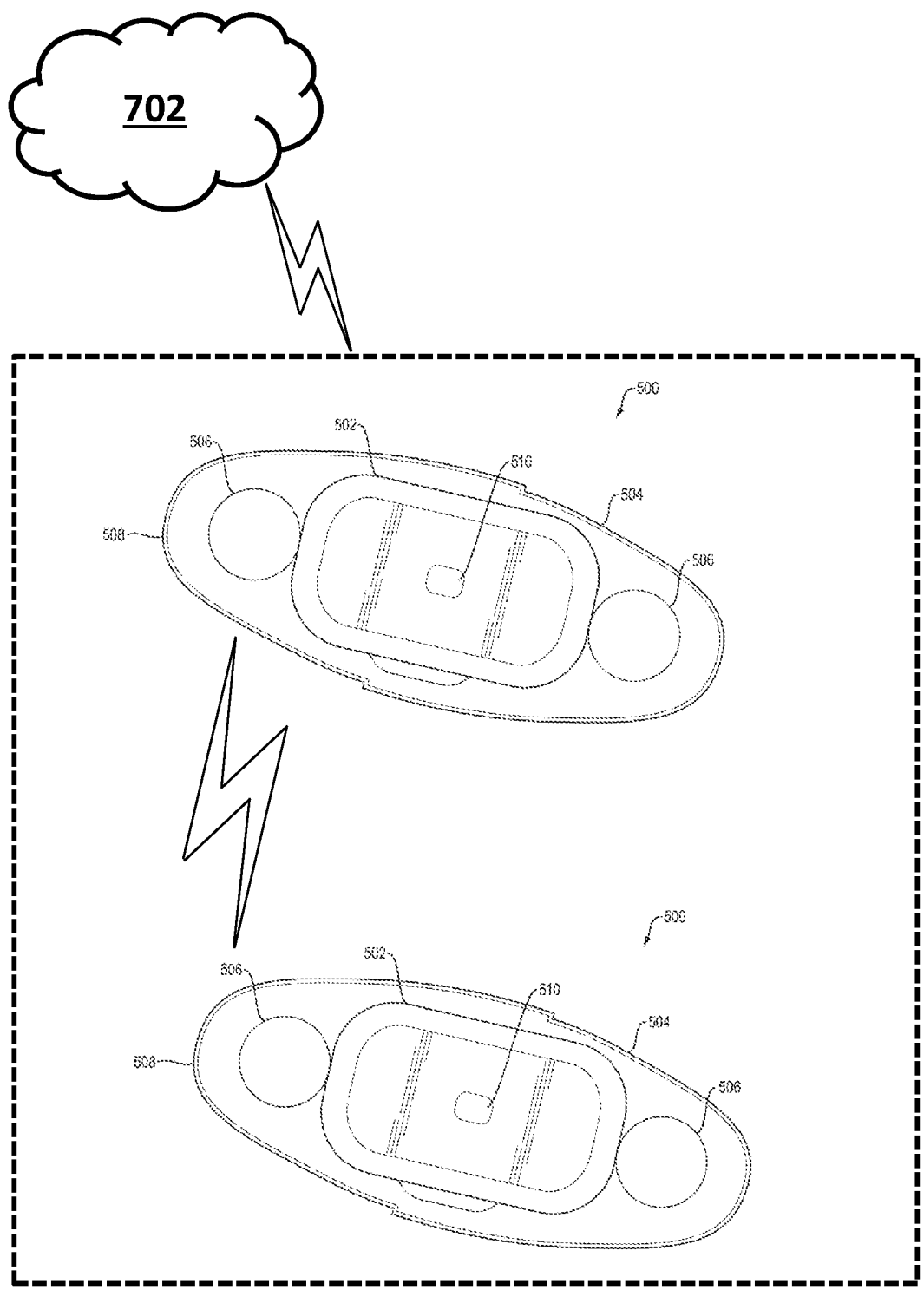
FIG. 8B is a depiction of two wearable health sensors in operative communication with one another and in further

Now referring to FIG. 8B, two wearable health sensors 500 are shown in operative communication with one another, allowing them to share data and otherwise capture data that a single sensor could not, and in further operative communication with a network 702. In embodiments, this network 702 may be a local-area network, such as might be used in a hospital setting for intra-hospital communications, while in other embodiments this network 702 may be a wide-area network, such as the internet.

Communications between wearable health sensors 500 and networks 702, directly, in embodiments, are enabled in a variety of ways, such as by the inclusion of a cellular data-capable modem and/or a WiFi enabled chipset in the wearable health sensor 500, although other methods of enabling network access would be known to one of ordinary skill in the art.

In embodiments, the network-enabled device 700 is a user device, such as a cellular phone with a data connection (e.g. to the internet). In embodiments, the wearable health sensor 500 connects to the network-enabled device 700 using Bluetooth®, or, more preferably, Bluetooth Low Energy® while, in other embodiments, a connection is made using zigbee, zwave, 802.11x, or other network protocols, as would be known to one of ordinary skill in the art.

In embodiments, communication between wearable health sensors 500 may be enabled via Bluetooth®, WiFi, cellular data, or a number of other means, which would be known to one of ordinary skill in the art.

Embodiments may further employ noise cancellation for multi-sensor 500 environments. In embodiments, noise cancellation may be achieved through the use of a wideband noise sensor, which is used to provide a measure of the background noise, combined with noise-cancelling algorithms. In some embodiments, five sensors 500 may be used to provide reverse phase noise cancellation capabilities.

Still even other embodiments group multiple 3-lead wearable health sensors 500, allowing the system to perform as a 6 or 12 lead ECG.

In embodiments, detection types include heart rate and heart rate variability, steps taken, respiratory rate, blood oxygen levels, skin temperature, body posture, glucose levels, fall detection, and GSR/EDA detection (change in amount of sweat in sweat glands).

The foregoing description of the embodiments of the invention has been presented for the purposes of illustration and description. Each and every page of this submission, and all contents thereon, however characterized, identified, or numbered, is considered a substantive part of this application for all purposes, irrespective of form or placement within the application. This specification is not intended to be exhaustive or to limit the invention to the precise form disclosed. Many modifications and variations are possible in light of this disclosure.

What is claimed is:

1. A detection and classification system, the system comprising:
   a sensor module configured to receive a biometric signal from a user;
   a feature detection module configured to receive the biometric signal and to analyze the biometric signal for repeating segments; and
   a signal feature classifier configured to receive the biometric signal and information regarding repeating segments therein from the feature detection module and to classify the biometric signal,
   wherein the system is configured to automatically notify a predetermined third-party of the occurrence of a predetermined classification contained within a reference model for diagnosis and follow-up,
   wherein the predetermined classification indicates the presence of a medical condition,
   wherein the reference model initially comprises a biological mechanism model and data corresponding to a general population,
   wherein the system is configured to update the reference model using data corresponding to the biometric signal received by the sensor module over time such that the reference model incorporates the user's baseline patterns, and
   wherein the process of updating the reference model using data corresponding to the biometric signal includes a supervised learning phase configured to create an inferred function that is used by the signal feature classifier to map data corresponding to the biometric signal received by the sensor module subsequent to the updating of the reference model as normal or abnormal.

2. The system of claim 1, wherein the biometric signal is an ECG signal, the feature detection module comprises a beat detection module, and the signal feature classifier comprises a beat classifier.

3. The system of claim 2, wherein the beat detection module is configured to detect a QRS complex.

4. The system of claim 1, wherein the feature detection module and the signal feature classifier are configured to receive the signal simultaneously.

5. The system of claim 1, wherein the signal classification is selected from the group consisting of normal, abnormal, and critical.

6. The system of claim 1, further comprising a derived feature detection module configured to further analyze the information generated by the feature detection module.

7. The system of claim 1, further comprising filters disposed between the sensor module and elements configured to receive the biometric signal therefrom, wherein said features are configured to strip irrelevant information from the biometric signal.

8. The system of claim 1, further comprising biometric sensors, wherein information therefrom is analyzed in parallel with information provided by the signal feature classifier.

9. The system of claim 8, wherein the information obtained from the biometric sensors is also taken into account by the feature classifier during signal classification.

10. The system of claim 1, wherein said system is further configured to transmit data upon which the classification was based with said notification.

11. The system of claim 1, wherein the biometric signal is down-sampled before being provided to the feature detection module and the signal feature classifier.

12. The system of claim 1 wherein the signal feature classifier is further configured to establish a baseline characterization of patient response.

13. The system of claim 1 wherein the biometric signal is ergodic.

14. A wearable detection and classification system, the system comprising:
a unitary housing configured to be worn by a patient, the unitary housing comprising:
an ECG sensor module configured to receive an ECG signal;
an ECG signal filter configured to process the received ECG signal;
a beat detection module configured to receive the processed ECG signal and to analyze the ECG signal for repeating segments;
a plurality of biometric sensors configured to acquire biometric data; and
a beat classifier configured to receive the processed ECG signal and information regarding repeating segments therein from the beat detection module, biometric data from at least one of the plurality of biometric sensors, and to classify the ECG signal as normal or abnormal based on a comparison of this information to a model ECG signal,
wherein the repeating segments are QRS complexes,
wherein the model ECG signal comprises a heartbeat mechanism model and a population-based model ECG signal that is combined with patient data obtained by the wearable detection and classification system over time such that the model ECG signal incorporates the patient's baseline patterns,
wherein the system is configured to assign a score to a classification based on how closely it matches a particular model,
wherein an abnormal classification indicates the presence of an ECG condition, and
wherein the system is configured to automatically notify a predetermined third-party of the occurrence of the abnormal classification and its associated score for formal diagnosis and follow-up.

15. The system of claim 14 wherein the individualized model is automatically created by the system using machine learning techniques, including a supervised learning phase requiring human assistance and an unsupervised learning phase wherein at least one machine learning algorithm and/or technique is used to draw inferences from datasets comprising individual sensor data, including raw ECG signal and derived feature information, without labeled responses, and
wherein the individualized model comprises personalized alterations to the behavior of the beat detector and beat classifier.

16. The system of claim 14 wherein machine learning comprises the application of non-parametric Bayesian methods that make use of infinite-dimensional mathematical structures.

17. The system of claim 14 wherein the processing of the received signal by the ECG signal filter, analyzing of the ECG signal for repeating segments by the beat detection module, and classification of the ECG signal as normal or abnormal by the beat classifier are performed by a computing resource external to the unitary housing.

18. The system of claim 14 wherein at least two of the unitary housings configured to be worn by a patient are worn by a single patient, wherein said at least two unitary housings are used and configured to gather overlapping information, and wherein the system is further configured to compared data generated by each unitary housing and identify and omit or average erroneous data.

19. The system of claim 14 further comprising a function button disposed on an exterior portion of the unitary housing and configured to cause data to be transmitted to the predetermined third-party upon activation.

* * * * *